(12) United States Patent
Hess et al.

(10) Patent No.: US 8,914,754 B2
(45) Date of Patent: Dec. 16, 2014

(54) DATABASE-DRIVEN CELL-TO-CELL RETICLE INSPECTION

(75) Inventors: Carl Hess, Los Altos, CA (US); John D. Miller, San Jose, CA (US); Shi Rui-Fang, Cupertino, CA (US); Chun Guan, Santa Clara, CA (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

(21) Appl. No.: 13/809,825

(22) PCT Filed: Apr. 23, 2012

(86) PCT No.: PCT/US2012/034681
§ 371 (c)(1),
(2), (4) Date: Jan. 11, 2013

(87) PCT Pub. No.: WO2012/148854
PCT Pub. Date: Nov. 1, 2012

(65) Prior Publication Data
US 2013/0111417 A1 May 2, 2013

Related U.S. Application Data

(60) Provisional application No. 61/479,002, filed on Apr. 26, 2011.

(51) Int. Cl.
*G06F 17/50* (2006.01)
*G01N 21/956* (2006.01)
*G01N 21/95* (2006.01)

(52) U.S. Cl.
CPC .......... *G06F 17/50* (2013.01); *G01N 21/95607* (2013.01); *G01N 21/9501* (2013.01)
USPC .................. 716/51; 716/50; 716/52; 716/53; 716/54; 716/56

(58) Field of Classification Search
USPC ..................... 716/50–56; 430/5, 30
See application file for complete search history.

(56) References Cited

U.S. PATENT DOCUMENTS

| | | | | |
|---|---|---|---|---|
| 6,175,417 B1 * | 1/2001 | Do et al. | ........................ | 356/392 |
| 6,347,150 B1 * | 2/2002 | Hiroi et al. | .................... | 382/149 |
| 6,411,378 B1 * | 6/2002 | Pike | .......................... | 356/237.5 |
| 6,757,621 B2 * | 6/2004 | Mizuno et al. | .................. | 702/35 |
| 7,065,239 B2 * | 6/2006 | Maayah et al. | ............... | 382/145 |
| 7,155,052 B2 * | 12/2006 | Geshel et al. | ................. | 382/144 |
| 7,269,816 B2 * | 9/2007 | Bevis | .............................. | 716/51 |
| 7,330,248 B2 * | 2/2008 | Sakai et al. | ................. | 356/237.4 |
| 7,332,359 B2 * | 2/2008 | Hamamatsu et al. | ........... | 438/14 |
| 7,734,082 B2 * | 6/2010 | Honda et al. | .................. | 382/145 |
| 7,949,178 B2 * | 5/2011 | Sakai et al. | ................. | 382/144 |
| 7,957,579 B2 * | 6/2011 | Hiroi et al. | ................. | 382/145 |
| 8,106,355 B1 * | 1/2012 | Lauber et al. | ................. | 250/307 |
| 8,126,259 B2 * | 2/2012 | Shimura | ...................... | 382/149 |
| 8,131,058 B2 * | 3/2012 | Shimura | ...................... | 382/149 |
| 8,270,700 B2 * | 9/2012 | Sakai et al. | ................. | 382/141 |
| 8,295,584 B2 * | 10/2012 | Sato et al. | ................. | 382/145 |
| 8,339,450 B2 * | 12/2012 | Takahashi | .................... | 348/126 |
| 2001/0033683 A1 * | 10/2001 | Tanaka et al. | ................. | 382/149 |

(Continued)

*Primary Examiner* — Nha Nguyen
(74) *Attorney, Agent, or Firm* — Suiter Swantz pc llo

(57) ABSTRACT

A semiconductor inspection apparatus identifies regions of a reticle or semiconductor wafer appropriate for cell-to-cell inspection by analyzing a semiconductor design database. Appropriate regions can be identified in a region map for use by offline inspection tools.

13 Claims, 4 Drawing Sheets

(56) References Cited

U.S. PATENT DOCUMENTS

| | | |
|---|---|---|
| 2005/0004774 A1 | 1/2005 | Volk et al. |
| 2005/0160394 A1* | 7/2005 | Bevis ............................. 716/19 |
| 2006/0019173 A1* | 1/2006 | Yamamoto ....................... 430/5 |
| 2006/0147104 A1* | 7/2006 | Horie et al. ................... 382/144 |
| 2006/0171593 A1* | 8/2006 | Hayakawa et al. ............ 382/209 |
| 2006/0280358 A1* | 12/2006 | Ishikawa ....................... 382/149 |
| 2008/0081385 A1 | 4/2008 | Marella et al. |
| 2008/0181484 A1 | 7/2008 | Litichever et al. |
| 2008/0315090 A1 | 12/2008 | Nakasuji et al. |
| 2009/0007030 A1* | 1/2009 | Nehmadi et al. ................. 716/4 |
| 2009/0297019 A1 | 12/2009 | Zafar et al. |
| 2010/0053319 A1* | 3/2010 | Sakai et al. ................... 348/125 |
| 2010/0128119 A1* | 5/2010 | Takahashi ..................... 348/126 |
| 2010/0215247 A1 | 8/2010 | Kitamura et al. |
| 2010/0259751 A1* | 10/2010 | Uto et al. ..................... 356/237.4 |

* cited by examiner

DATABASE-DRIVEN CELL-TO-CELL RETICLE INSPECTION

PRIORITY

The present application is related to and claims the benefit of the earliest effective filing date from International Application No. PCT/US2012/034681, filed Apr. 23, 2012, which claims priority to U.S. Provisional Application Ser. No. 61/479,002, filed Apr. 26, 2011, which are all incorporated herein by reference.

FIELD OF THE INVENTION

The present invention is directed generally toward inspection in semiconductor processing, and more particularly to cell-to-cell inspection processes.

BACKGROUND OF THE INVENTION

Inspection and metrology technologies are conventionally used in semiconductor fabrication facilities for material monitoring, disposition, yield prediction, and yield management. Wafers are inspected at various stages of production using both in-line and off-line processes. Cell-to-cell inspection is a mode wherein locally repeating structures are compared to each other, and any noted difference is declared to be a defect. Cell-to-cell inspection is used in both wafer and reticle inspection. This modality has advantages in that the reference data is very closely spaced to the test region so that the inspection tool does not need to be particularly stable to successfully employ this approach.

Recent changes in lithographic approaches make cell-to-cell inspection more problematic. Model-based Optical-Proximity-Correction (OPC) for optical masks and Flare Correction for extreme ultraviolet (EUV) masks can lead to very subtle differences in the design of nearly repeating patterns. These changes may include, for example, a very small jog in a long straight line with no apparent purpose. Existing methods of determining whether a region is sufficiently repeating for the application of a cell-to-cell detector uses the images themselves. This means that a subtle design difference between cells can easily be declared to be a defect rather than an intentional design feature. It is this false defect mechanism that can limit the sensitivity and applicability of the cell-to-cell defect detectors.

Consequently, it would be advantageous if an apparatus existed that is suitable for identifying cells in a reticle appropriate for cell-to-cell inspection.

SUMMARY OF THE INVENTION

Accordingly, the present invention is directed to a novel method and apparatus for identifying cells in a reticle appropriate for cell-to-cell inspection.

One embodiment of the present invention is a method for determining which cells in a reticle are suitable for cell-to-cell inspection by analyzing a semiconductor design database directly. The method may include producing a region map indicating which cells are valid for cell-to-cell inspection.

Another embodiment of the present invention is a cell-to-cell inspection apparatus that performs an analysis of a semiconductor design database to determine valid cell-to-cell inspection candidates.

Another embodiment of the present invention is a cell-to-cell inspection apparatus that performs an analysis of a region map indicating valid cell-to-cell inspection candidates. The region map is produced based on an analysis of a semiconductor design database.

It is to be understood that both the foregoing general description and the following detailed description are exemplary and explanatory only and are not restrictive of the invention claimed. The accompanying drawings, which are incorporated in and constitute a part of the specification, illustrate an embodiment of the invention and together with the general description, serve to explain the principles.

BRIEF DESCRIPTION OF THE DRAWINGS

The numerous objects and advantages of the present invention may be better understood by those skilled in the art by reference to the accompanying figures in which.

DETAILED DESCRIPTION OF THE INVENTION

Reference will now be made in detail to the subject matter disclosed, which is illustrated in the accompanying drawings. The scope of the invention is limited only by the claims; numerous alternatives, modifications and equivalents are encompassed. For the purpose of clarity, technical material that is known in the technical fields related to the embodiments has not been described in detail to avoid unnecessarily obscuring the description.

Figure 1:
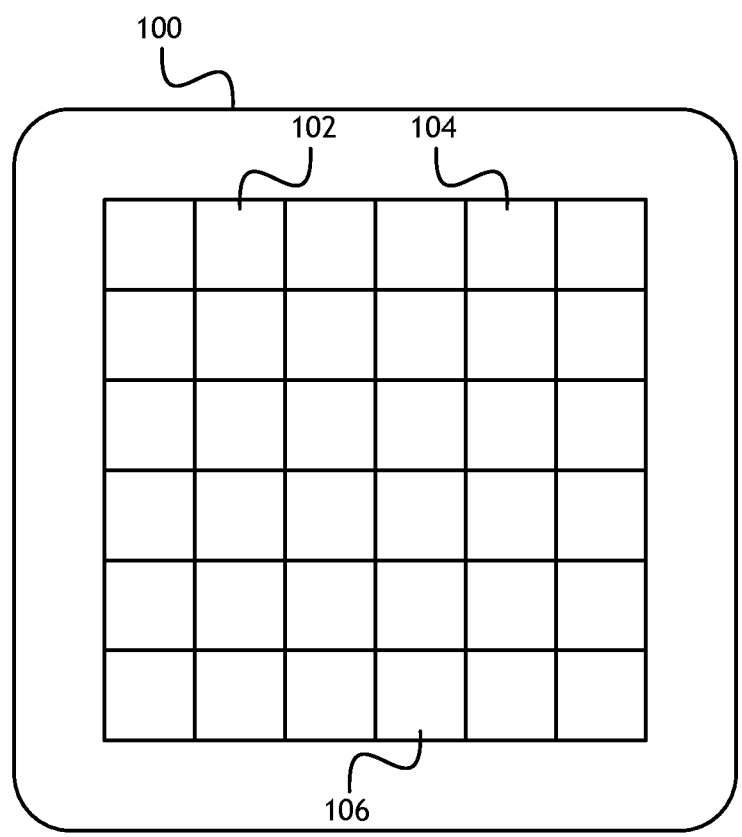
FIG. 1 shows a block diagram of a reticle.

Referring to FIG. 1, a block diagram representation of a reticle 100 is shown. During lithographic fabrication, one or more reticles 100 are used to construct electronic components onto a semiconductor wafer through methods known in the art. The electronic components may be organized into groups called cells 102, 104, 106. Some cells may comprise identical components in identical orientations such that a properly aligned comparison of two such cells, for example a first cell 102 and a second cell 104, would reveal a defect in either the first cell 102 or the second cell 104.

However, a reticle 100 may also contain cells 102, 104, 106 that are very similar but not identical. A semiconductor fabrication process may require certain cells 102, 104, 106 in a reticle 100, for example a third cell 106, to be slightly different as compared to other cells, for example the first cell 102 and the second cell 104, even though all three cells 102, 104, 106 may contain substantially the same components in substantially the same orientation. Processes such as optical proximity correction may alter the design of certain cells to correct for potential irregularities in the fabrication process. A comparison of the first cell 102 and the third cell 106 may indicate a defect even if both cells 102, 106 were fabricated properly according to the intended design (false defects).

When using real inspection images in autocorrelation analysis to determine the similarity (repeatability) of cells, noise in the images may fundamentally limit the fidelity of the autocorrelation. The system must therefore define some threshold level for repeatability. The system may accept imperfectly repeating patterns thereby leading to false defects, or reject repeating patterns containing a defect, thereby leading to lower sensitivity because the cell-to-cell detector is disabled. These factors are currently the dominant source of false defects in cell-to-cell inspections and limit the sensitivity of the inspection process. The present invention may be employed to remove the possibility of such false defects.

Figure 2:
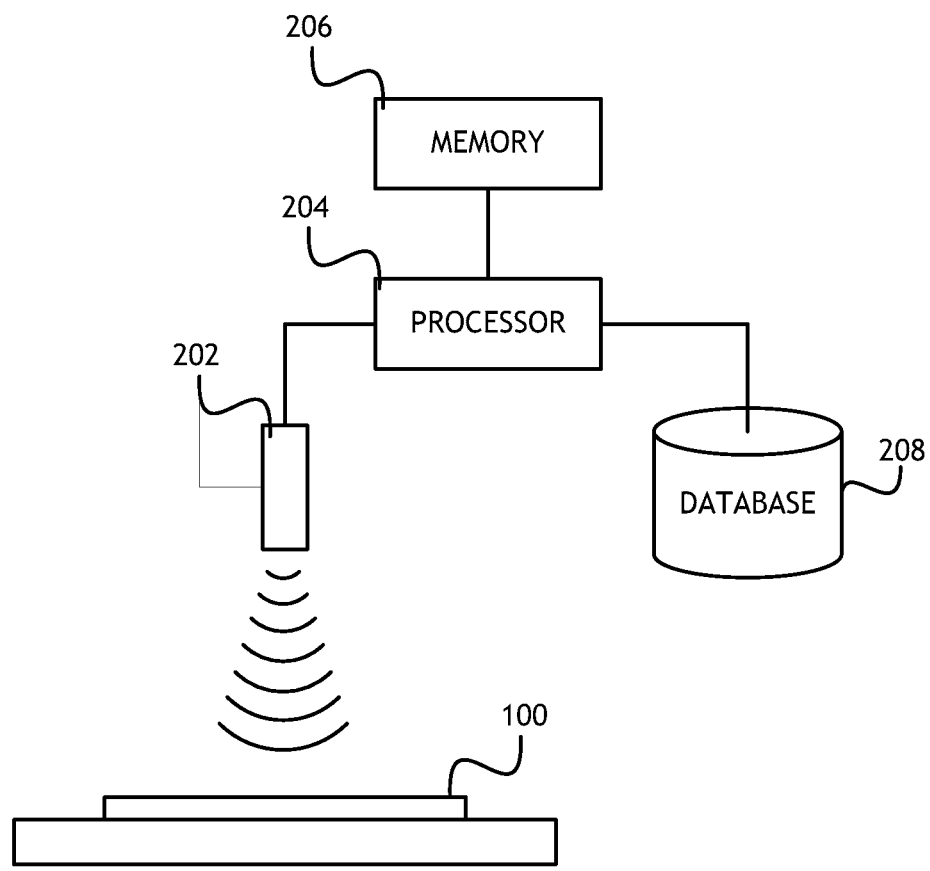
FIG. 2 shows a block diagram of a system suitable for performing cell-to-cell inspection of a reticle.

Referring to FIG. 2, an apparatus for producing a region map of a reticle 100, and for performing cell-to-cell inspections of a reticle 100 is shown. The apparatus may include a processor 204, memory 206 connected to the processor 204 and a semiconductor design database 208 connected to the processor 204. The processor 204 may analyze the semiconductor design database 208 to identify cells intended by design to have identical structure, which are therefore appropriate for cell-to-cell inspection. The processor 204 may then produce a region map indicating cells identified from the semiconductor design database 208 that are appropriate for cell-to-cell comparison. The processor 204 may also identify reference points from the semiconductor design database 208 and include those reference points in the region map so that the region map may be properly aligned with an actual fabricated reticle 100.

Using the semiconductor design database 208, the processor 204 may analyze the repeatability of semiconductor structures using processes such as autocorrelation analysis. Peaks in the autocorrelation may indicate repeating patterns of various fidelity and size. With a rendered semiconductor design database 208, there is no measurement noise at all. The fidelity of the rendering is limited by the accuracy of the calculations in the rendering, driven by precision of the numbers and potentially by the rendering pixel size. This allows the processor 204 to set a threshold for choosing whether to apply cell-to-cell inspection that is well below the inspection sensitivity. Furthermore, since the calculations are performed on the semiconductor design database 208, the presence of an actual defect may not taint the result. By this method, the processor 204 may produce a region map of appropriate cell-to-cell inspection regions of a reticle 100. The region map may be stored in a memory for use by an inspection device.

The apparatus of FIG. 2 may further include an imaging device 202 for imaging a reticle 100. The reticle 100 may be produced according to the semiconductor design database 208. The processor 204 may read a region map stored in memory 206; the region map indicating regions of the reticle 100 suitable for cell-to-cell inspection. The processor 204 may then image the reticle 100 using the imaging device 202. The processor 204 may then orient the region map and the image of the reticle 100 based on corresponding reference points. The processor 204 may then perform cell-to-cell inspection on regions of the reticle 100 identified by the region map as appropriate for cell-to-cell inspection.

The processor 204 may further perform some appropriate inspection process on regions indentified by the region map as inappropriate for cell-to-cell inspection because those regions would be likely to produce false defects.

The present invention incorporates both rendering and analyzing a semiconductor design database 208 to produce a region map, and applying the region map to a reticle 100 image. One skilled in the art may appreciate that the processes for producing the region map may be performed separate in time and space from the processes for applying the region map.

Therefore, in an alternative embodiment, the apparatus may include a processor 204, memory 206 connected to the processor 204 and an imaging device 202 connected to the processor 204. The processor 204 may read a region map stored in memory 206; the region map indicating regions of a reticle 100 suitable for cell-to-cell inspection. The processor 204 may then image the reticle 100 using the imaging device 202. The processor 204 may then orient the region map and the image of the reticle 100 based on corresponding reference points. The processor 204 may then perform cell-to-cell inspection on regions of the reticle 100 identified by the region map as appropriate for cell-to-cell inspection. The processor 204 does not need to be connected to a semiconductor design database 208 at the time of inspection.

One skilled in the art may appreciate that while the forgoing discussion focused on reticle 100 inspection, all of the same principles, processes and structures may be equally applicable to cell-to-cell inspection of semiconductor wafers.

Figure 3:
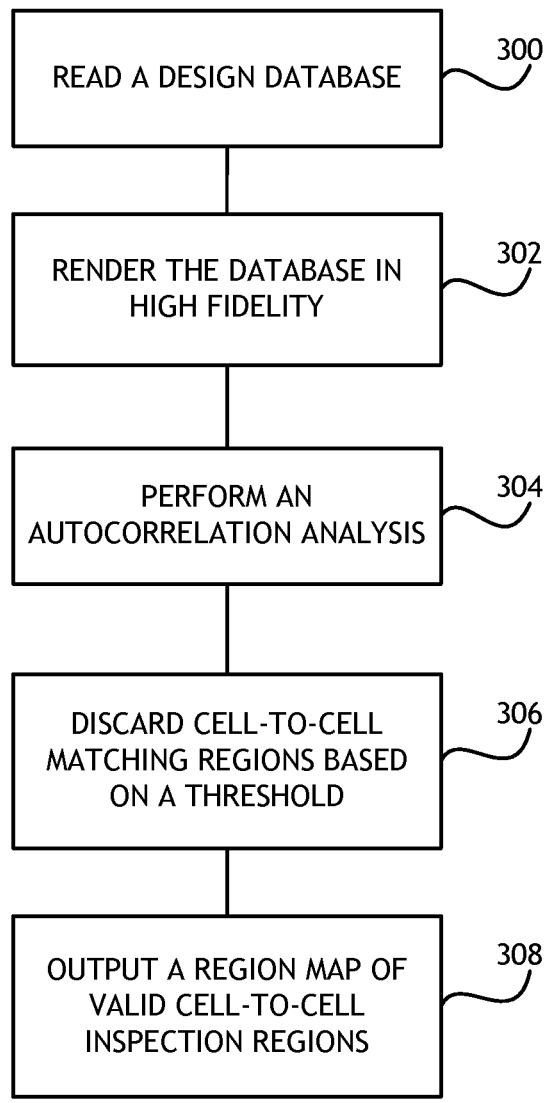
FIG. 3 shows a flowchart for a method for determining regions in a reticle appropriate for cell-to-cell inspection.

Referring to FIG. 3, a flowchart for inspecting a reticle is shown. A processor may read 300 a semiconductor design database. The processor may then render 302 the semiconductor design database in high fidelity. In this embodiment high fidelity refers the noise level of the resulting image as compared to images generally produced by inspection hardware at the time of inspection.

Alternatively, instead of examining the rendered semiconductor design database images in high fidelity, the processor may use a particular characteristic of repeating patterns. In a semiconductor design database there may be a "hierarchy" which indicates patterns that are exactly repeating in the semiconductor design database. The pattern may only be described in detail one time, and then there may be an indication of all the places where the pattern is located. Hierarchy is used as a means of compressing the semiconductor design database data. A process can analyze a semiconductor design database for the hierarchy that is employed to determine those regions that are truly repeating.

Where a processor renders the semiconductor design database, the processor may then perform 304 an autocorrelation analysis to determine regions of the semiconductor design database that are truly repeating and discard 306 cell-to-cell matching regions based on a threshold of the autocorrelation analysis. In some embodiments, such as when the processor is not currently conducting an inspection, the processor may output 308 a region map of valid cell-to-cell inspection regions. Alternatively, where the processor is currently performing an inspection, the processor may directly utilize the identified regions to perform cell-to-cell inspection without producing a region map, or producing the region map as a transitory data structure.

Figure 4:
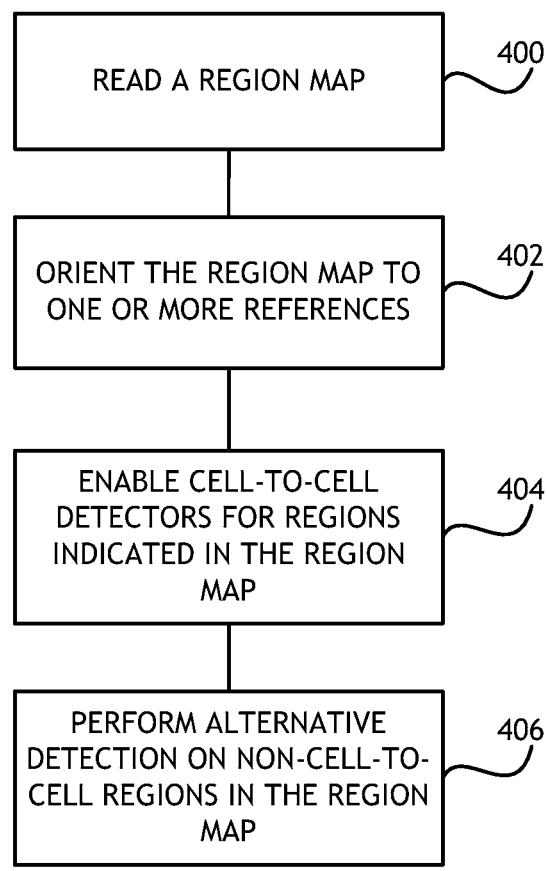
FIG. 4 shows a flowchart of a method for using a region map to conduct cell-to-cell inspections of a reticle.

Referring to FIG. 4, a flowchart for utilizing a region map in an inspection process is shown. Where an inspection apparatus is not connected to a semiconductor design database, a processor in the inspection apparatus may read 400 a region map identifying regions in a reticle appropriate for cell-to-cell inspection. The processor may then orient 402 the region map to an image of a reticle based on reference points common to the region map and reticle. The processor may then enable cell-to-cell inspection of the regions of the reticle identified as appropriate for cell-to-cell inspection in the region map. For those regions not identified as appropriate for cell-to-cell inspection in the region map, or specifically identified as inappropriate for cell-to-cell inspection, the processor may perform 406 an alternative method of defect detection known in the art.

It is believed that the present invention and many of its attendant advantages will be understood by the foregoing description, and it will be apparent that various changes may be made in the form, construction, and arrangement of the components thereof without departing from the scope and spirit of the invention or without sacrificing all of its material advantages. The form herein before described being merely an explanatory embodiment thereof, it is the intention of the following claims to encompass and include such changes.

What is claimed is:

1. A inspection apparatus comprising:
a processor;
memory connected to the processor;
an imaging device connected to the processor, configured for cell-to-cell inspection of at least one of a reticle or a semiconductor wafer; and
computer executable program code configured to execute on the processor,
wherein the computer executable program code is configured to:
perform cell-to-cell inspection of regions of the reticle or semiconductor wafer identified as appropriate for cell-to-cell inspection based on a semiconductor design database; and
prohibit cell-to-cell inspection of regions of the reticle or semiconductor wafer identified as inappropriate for cell-to-cell inspection based on the semiconductor design database, regions inappropriate for cell-to-cell inspection including substantially similar elements wherein one of said substantially similar elements is altered by optical proximity correction;
wherein the executable program code is further configured to analyze the semiconductor design database to identify regions of the reticle or semiconductor wafer appropriate for cell-to-cell inspection; and
wherein analyzing the semiconductor design database comprises at east at least one of autocorrelation analysis or hierarchy analysis.

2. The apparatus of claim 1, wherein the computer executable program code is further configured to perform an inspection process other than cell-to-cell inspection on regions of the reticle or semiconductor wafer identified as inappropriate for cell-to-cell inspection based on the semiconductor design database.

3. The apparatus of claim 1, wherein:
the memory is configured to store a region map of the reticle or semiconductor wafer;
the region map is configured to identify regions of the reticle or semiconductor wafer appropriate for cell-to-cell inspection;
the computer executable program code is further configured:
to read the region map; and
orient the region map to one or more references on the reticle or semiconductor wafer.

4. The apparatus of claim 3, wherein the computer executable program code is further configured to prohibit cell-to-cell inspection of regions of the reticle or semiconductor wafer identified in the region map as inappropriate for cell-to-cell inspection.

5. The apparatus of claim 1, wherein the computer executable program code is further configured to perform an inspection process other than cell-to-cell inspection on regions of the reticle or semiconductor wafer identified in the region map as inappropriate for cell-to-cell inspection.

6. A computer apparatus comprising:
a processor;
memory connected to the processor, configured to store a region map of a reticle or semiconductor wafer; and
computer executable program code,
wherein the computer executable program code is configured to:
read a semiconductor design database;
analyze the semiconductor design database to identify regions appropriate for cell-to-cell inspection;
produce a region map of valid cell-to-cell inspection regions based on the analysis of the semiconductor design database; and
prohibit cell-to-cell inspection of regions of the reticle or semiconductor wafer identified as inappropriate for cell-to-cell inspection based on the semiconductor design database, regions inappropriate for cell-to-cell inspection including substantially similar elements wherein one of said substantially similar elements is altered by optical proximity correction;
wherein the computer executable program code is further configured to render the semiconductor design database; and
wherein the computer executable program code is further configured to perform an autocorrelation analysis.

7. The apparatus of claim 6, wherein the computer executable program code is further configured to discard cell-cell matching regions based on an autocorrelation threshold.

8. The apparatus of claim 6, further comprising a semiconductor imaging device connected to the processor, configured for cell-to-cell inspection of the reticle or semiconductor wafer.

9. The apparatus of claim 8, wherein the computer executable program code is further configured to orient the region map to one or more references on the reticle or semiconductor wafer.

10. The apparatus of claim 9, wherein the computer executable program code is further configured to perform an inspection process other than cell-to-cell inspection on regions of the reticle or semiconductor wafer identified in the region map as invalid for cell-to-cell inspection.

11. A method of inspection comprising:
analyzing, via a computer processor, a semiconductor design database to identify regions appropriate for cell-to-cell inspection;
producing, via a computer processor, a region map of regions appropriate for cell-to-cell inspection based on the analysis of the semiconductor design database; and
prohibiting cell-to-cell inspection of regions of the reticle or semiconductor wafer identified as inappropriate for cell-to-cell inspection based on the semiconductor design database, regions inappropriate for cell-to-cell inspection including substantially similar elements wherein one of said substantially similar elements is altered by optical proximity correction; and
wherein analyzing the semiconductor design database further comprises one of an autocorrelation analysis or a hierarchy analysis.

12. The method of claim 11, further comprising:
orienting the region map to one of a reticle or a semiconductor wafer; and
enabling cell-to-cell inspection for regions identified in the region map as appropriate for cell-to-cell inspection.

13. The method of claim 11, further comprising performing an inspection other than cell-to-cell inspection on regions identified in the region map as inappropriate for cell-to-cell inspection.

* * * * *